United States Patent [19]

Yasui et al.

[11] 4,122,023

[45] * Oct. 24, 1978

[54] SYNTHETIC SATURATED OILS, AND THEIR PRODUCTION AND USE

[75] Inventors: Seimei Yasui, Takarazuka; Hiroshi Sato, Toyonaka, both of Japan

[73] Assignee: Sumitomo Chemical Company, Limited, Osaka, Japan

[*] Notice: The portion of the term of this patent subsequent to Nov. 29, 1994, has been disclaimed.

[21] Appl. No.: 841,669

[22] Filed: Oct. 13, 1977

Related U.S. Application Data

[63] Continuation-in-part of Ser. No. 689,689, May 25, 1976, Pat. No. 4,060,492.

[30] Foreign Application Priority Data

May 26, 1975 [JP] Japan .................................. 50-63266
Jun. 4, 1975 [JP] Japan .................................. 50-67764
Nov. 5, 1975 [JP] Japan .................................. 50-133268

[51] Int. Cl.$^2$ ............................................. C10M 1/18
[52] U.S. Cl. .................................. 252/59; 260/676 R; 260/680 B; 260/683.9; 424/64; 424/358
[58] Field of Search ............ 260/676 R, 680 B, 683.9; 252/59; 424/64, 358

[56] References Cited

U.S. PATENT DOCUMENTS

| | | | |
|---|---|---|---|
| 3,113,986 | 12/1963 | Breslow et al. | 260/683.9 |
| 3,557,075 | 1/1971 | Gaeth | 260/680 B |
| 3,801,508 | 4/1974 | Meier et al. | 252/59 |
| 3,835,053 | 9/1974 | Meier et al. | 252/59 |
| 3,965,019 | 6/1976 | St. Clair et al. | 252/59 |

FOREIGN PATENT DOCUMENTS

2,453,871 0000 Fed. Rep. of Germany.
2,453,872 0000 Fed. Rep. of Germany.

OTHER PUBLICATIONS

Prager et al. "Beilsteins Handbuch der Organischen Chemie", Syst. No. 10, p. 168.
Chem. Abs. 1967–1971 Formula Index.

*Primary Examiner*—C. Davis
*Attorney, Agent, or Firm*—Birch, Stewart, Kolasch and Birch

[57] ABSTRACT

Synthetic saturated oils useful as materials for lubricating oils and cosmetics and prepared by hydrogenation of low molecular weight polyisoprene having the 1,4 structure of at least 70% in the main chains and a number average molecular weight of about 290 to 3,000.

13 Claims, No Drawings

SYNTHETIC SATURATED OILS, AND THEIR PRODUCTION AND USE

This is a continuation-in-part application of our co-pending application Ser. No. 689,689, filed May 25, 1976, now U.S. Pat. No. 4,060,492.

The present invention relates to synthetic saturated oils, and their production and use. More particularly, it relates to novel synthetic saturated oils, their production from low molecular weight polyisoprene and compositions comprising them.

As lubricating oils, there are known petroleum lubricating oils, synthetic lubricating oils, fatty oils, etc. For the practical use, these oils are usually blended with various additives for improving their properties such as viscosity index improvers, flow point depressants, anti-corrosive agents and carbonization inhibitors. On lubricating oils used for the engines of jet planes, no lowering of physical properties between the two extremes of temperature is required. In case of lubricating oils for precision machines such as watches, a high viscosity index and a low flow point are considered as important. Automatic change gears also require high-quality lubricating oils. As lubricating oils meeting these requirements, there are proposed some synthetic oils. An example of them is oils obtained by polymerization of α-olefins using Lewis acid (e.g. aluminum chloride, aluminum bromide) as a catalyst. During the polymerization, however, isomerization takes place so as to change the branching of the polymers, thus giving no polymer having a high viscosity index. Another example is oils obtained by polymerization of α-olefins using a coordination anionic polymerization catalyst. These oils indicate usually a viscosity index of more than 130, a flash point of higher than 210° C. and a flow point of lower than −50° C. However, with such flow point, they can not pass, for instance, the standards for hydraulic oils for airplanes under the American Military Standards (hereinafter referred to as "MIL") H-83282 and the standards for jet engine oils under MIL H-7807. In order to meet these standards, there is proposed a method for producing lubricating oils by polymerizing α-olefins having not less than 5 carbon atoms (e.g. octene-1, decene-1) in the presence of a catalyst composition comprising aluminum chloride and lithium aluminum hydride, followed by fractional distillation and hydrogenation. While the thus obtained saturated oils pass the said standards, there is still a demand to lubricating oils having a higher viscosity index.

On the other hand, there are known various synthetic oils for cosmetics such as liquid paraffin, glycerol and polyethylene glycol. However, these synthetic oils are inferior to squalene, which results from purification of shark oil, in penetration and absorption into the skin of human body. Squalene has the structure corresponding to the 1,4 polymerization product of isoprene, all the double bonds present therein having the trans configuration. Because of the presence of many double bonds, squalene is apt to be oxidized with air, whereby an offensive odor is generated and sometimes harmful substances to human body are produced. This drawback can be overcome by subjecting squalene to hydrogenation so as to make an unsaturation degree of zero. The resulting hydrogenation product, i.e., squalene, is superior in weathering resistance and penetration into and non-toxicity to the skin of human body. Since, however, squalene is a product isolated from sharks, it has become expensive with the reduction in the catch of sharks. Thus, the appearance of a synthetic oil comparable to squalene or squalene in various favorable properties on the use for cosmetics has been highly demanded.

In order to provide synthetic oils suitable for various uses including lubricating oils and cosmetics, various attempts have been made up to the present time. Some of them are disclosed in Japanese Patent Publication (examined) No. 35,984/1974, Japanese Patent Publication (unexamined) Nos. 85,243/1974, 117,413/1974 and 133,302/1974, etc.

In Japanese Patent Publication (examined) No. 35,984/1974, the method comprises heat-polymerization of isoprene in the presence of a solid acid catalyst, and the isoprene may polymerize not in the straight form (i.e., 1,4 polymerization) but in the branched forms (e.g. cyclic polymerization, 3,4 polymerization, 1,2 polymerization). The polymerized isoprenes thus obtained have the structure in which an isopropenyl group, a vinyl group and a six-membered ring are linked to the side chains, and therefore they have a higher viscosity and a poorer flowing property than do the oils resulting from hydrogenation of natural straight terpenes.

In Japanese Patent Publication (unexamined) No. 85,243/1974, synthetic oils are produced by hydrogenation of low molecular weight polymers resulting from the polymerization of olefins having 4 carbon atoms such as isobutylene, butadiene and butene-1. The oils thus obtained have a high viscosity even if their molecular weight is low and are inferior to natural oils in flowing property.

Japanese Patent Publication (unexamined) Nos. 117,413/1974 and 133,302/1974 disclose a method wherein squalene is synthetized by coupling geranyl acetone and hexahydropseudoionone, followed by dehydration and hydrogenation. The produced oils have a flowing property close to that of natural squalene. However, this method is disadvantageous in requiring not only expensive starting materials (e.g. geranyl acetone and hexahydropseudoionone) but also many reaction stages (i.e., coupling, dehydration and hydrogenation).

As the result of the extensive study, it has now been found that the hydrogenation of certain low molecular weight polyisoprene affords synthetic saturated oils, of which fractional distillation products have a wide variety of flow characteristics suitable for various uses including lubricating oils and cosmetics and some of them are quite similar to squalene in physical properties.

According to the present invention, synthetic saturated oils are produced by hydrogenation of low molecular weight polyisoprene having the 1,4 structure of at least 70% in the main chains and a number average molecular weight of about 290 to 3,000.

The starting material in the method of this invention is low molecular weight polyisoprene as defined above. When the 1,4 structure in the main chains is less than 70%, the resulting hydrogenation product can hardly flow or can not have a low viscosity. In general, the use of low molecular weight polyisoprene having a higher content of 1,4 structure affords the hydrogenation product of lower viscosity. Also, the use of the one having a higher content of cis structure gives the hydrogenation product of lower viscosity.

The low molecular weight polyisoprene suitable as the starting material may be produced by conventional procedures. For instance, such polyisoprene is obtainable by polymerization of isoprene in the presence of an α-olefin using a catalyst composition comprising an organometallic compound and a nickel compound with or without an electron donor as described in Japanese Patent Publication (unexamined) No. 115,189/1974. The molecular weight of the polymer to be produced can be readily regulated by controlling the amounts of the α-olefin, the organometallic compound, the nickel compound and the electron donor. Further, for instance, the suitable polyisoprene may be produced by living polymerization of isoprene by the use of a complex comprising metallic lithium and naphthalene in an inert solvent such as hexane as described in Journal of Polymer Science, 56, 449. Furthermore, for instance, the suitable polyisoprene may be produced by polymerization of isoprene using lithium salts as described in Japanese Patent Publication (unexamined) Nos. 35,102/1975, 46,606/1975 and 34,382/1975. Stillmore, for instance, the suitable polyisoprene may be produced by polymerization of isoprene in the presence of a radical initiator.

The low molecular weight polyisoprene thus produced may be separated as liquid polymer from the reaction mixture by a conventional separation procedure. For instance, the catalyst for polymerization is deactivated by treatment with methanol, ethanol, propanol, n-amyl alcohol, water or the like and then eliminated by washing with an aqueous solution of acid (e.g. hydrochloric acid, sulfuric acid, nitric acid, formic acid, acetic acid, oxalic acid). The resultant mixture is neutralized with an aqueous alkaline solution, washed with water and then concentrated under reduced pressure for removal of the solvent, whereby the liquid polymer is obtained.

Hydrogenation of the liquid polymer thus obtained may be carried out by treatment with hydrogen in the presence of a hydrogenation catalyst, usually at a temperature of about 50° to 350° C. for about 1 to 100 hours under a hydrogen pressure of about 5 to 300 kg/cm². The treatment may be carried out in the presence or absence of an inert solvent such as alcohols (e.g. methanol, ethanol), ketones (e.g. acetone, methylethylketone), aliphatic hydrocarbons (e.g. heptane, hexane, pentane, cyclohexane) or their mixtures. As the hydrogenation catalyst, there may be used any conventional one such as nickel (e.g. Raney nickel, nickel on diatomaceous earth, Urushibara nickel), palladium and platinum. After completion of the hydrogenation, the catalyst and the solvent are removed from the reaction mixture by usual methods, and the distillation of the reaction mixture under reduced pressure affords the hydrogenated product of the liquid polymer.

The thus obtained hydrogenated liquid polymer, i.e., the synthetic saturated oil of the invention, has a broad molecular weight distribution, comprises polymers ranging from low molecular weight ones to high molecular weight ones and shows generally the following physical properties:

Appearance: colorless, transparent, odorless;
Boiling point: B.P. (at 760 mmHg) $\geq$ 250° C.;
Specific gravity: $0.80 \leq d^{20} \leq 0.92$;
Refractive index: $1.44 \leq n_D^{20} \leq 1.50$;
Viscosity: $5 \text{ cp} \leq \eta^{25° C.} \leq 10^5 \text{ cp}$.

The main components in such hydrogenation liquid polymer are hydrogenated polyisoprenes substantially representable by the formula:

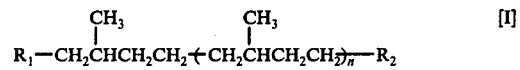

wherein $R_1$ is hydrogen or alkyl having 1 to 8 carbon atoms, $R_2$ is hydrogen, ethyl or isopropyl and $R_1$ and $R_2$ are not hydrogens at the same time and $n$ is an integer of 3 to 40, preferably 4 to 20. When, for instance, the hydrogenated liquid polymer is produced by hydrogenation of the liquid polymer according to the method described in Japanese Patent Publication (unexamined) No. 115,189/1974, its major components are the ones represented by the formula [I] wherein $R_1$ is hydrogen and $R_2$ is ethyl or isopropyl. Further, the hydrogenated liquid polymer produced by hydrogenation of a liquid polymer obtained by polymerization of isoprene in the presence of lithium or $C_1$-$C_8$ alkyl lithium may comprise as its major components the ones represented by the formula [I] wherein $R_1$ is hydrogen or $C_1$-$C_8$ alkyl and $R_2$ is hydrogen. Furthermore, for instance, the hydrogenated liquid polymer obtained by the process described in Example 2 as hereinafter presented contains as the major components the ones represented by the formula [I] wherein $R_1$ is hydrogen and $R_2$ is isopropyl and, when subjected to rectification and gel permeation chromatography, affords the following substances:

| n | Molecular weight* | Viscosity at 25° C (cp) | Boiling point at 0.15 Torr (° C) | Specific gravity $d^{20}$ | Refractive index $n_D^{20}$ |
|---|---|---|---|---|---|
| 3 | 316 | 8.0 | 143 | 0.8051 | 1.4490 |
| 4 | 380 | 15.6 | 172 | 0.8092 | 1.4529 |
| 5 | 450 | 28 | 195 | 0.8125 | 1.4560 |
| 6 | 525 | 45 | 213 | 0.8160 | 1.4585 |
| 7–9 | 670 | 105 | 230–270 | 0.8208 | 1.4630 |
| 10–12 | 840 | 250 | 280–320 | 0.8263 | 1.4683 |

Note*
*determined by the vapor pressure osmometry method

The hydrogenated liquid polymer may be separated by a conventional procedure such as fractional distillation into the initial fraction (30° C. $\leq$ B.P./1 mmHg $\leq$ 150° C.) having a low viscosity, the middle fraction (150° C. < B.P./1 mmHg $\leq$ 450° C.) having a medium viscosity and the residual matter (450° C. < B.P./1 mmHg) having a high viscosity. The fraction, having a molecular weight smaller than about 290, has rather slight irritation to the skin for long use for cosmetics and a low flash point in use for lubricating oil. Therefore, the fraction, having a molecular weight smaller than 290, is not included in the present invention. These fractions are applied to various uses such as machine oils for precision machines (e.g. watches, measuring instruments, telephones), engine oils for automobiles and lubricating oils for jet planes and propeller planes depending on their viscosities and flash points. On these uses, they may be used alone or in combination with conventional additives such as viscosity index improvers, flow point depressants, anti-corrosive agents and carbonization inhibitors.

As well known, cosmetics are generally prepared by admixing together oil soluble materials such as vegetable oils (e.g. beeswax, vegetable wax, cetyl alcohol), stearic acid, lanolin, castor oil, olive oil), mineral oils (e.g. paraffin, liquid paraffin, vaseline, ceresine) and animal oils (e.g. squalene), water-soluble materials such as ethanol, glycerol, propylene glycol, polyethylene glycol, methyl cellulose, hydroxyethyl cellulose, polyvinyl alcohol, polyvinyl pyrrolidone, tragacanth gum and acacia gum, surfactants, coloring materials such as inorganic pigments (e.g. zinc stearate, ultramarine, titanium oxide, talc, kaolin), organic dyes and natural coloring matters, antioxidants, perfumes and water.

The hydrogenated liquid polymer obtained by this invention and the fractions therefrom may be used as oil soluble materials in the said cosmetics in the form of milky lotions, creams, stick pomades and the like. Since they are already hydrogenated, no deterioration in quality will be caused on those cosmetics.

Practical and presently preferred embodiments of the present invention are illustratively shown in the following Examples.

EXAMPLE 1

The atmosphere in a 1.5-liter stainless steel autoclave (20 kg/cm$^2$ proof) equipped with a stirrer was replaced by nitrogen gas. Thereafter, 300 ml of anhydrous toluene and 136 g of anhydrous isoprene were charged into the autoclave under the stream of nitrogen. The mixture was cooled to −50° C., and 4 ml of a toluene solution containing 0.1 mol/liter of nickel naphthenate, 4 ml of a toluene solution containing 1 mol/liter of ethylaluminum sesquichloride, 4 ml of a toluene solution containing 0.02 mol/liter of triphenyl phosphine and 64 g of propylene were added thereto, followed by polymerization at 60° C. for 6 hours. The polymerization was stopped by adding 10 ml of a 10% solution of isopropanol in toluene under pressure, followed by stirring for 10 minutes. Unreacted propylene and isoprene were purged in a draft, and the reaction mixture was washed for 5 hours with 800 ml of an aqueous hydrochloric acid solution (pH 1.6) in a 2-liter glass flask and allowed to stand. The aqueous layer was removed, and the oily layer was mixed with 800 ml of an aqueous sodium hydroxide solution (pH 12) for 1 hour and allowed to stand. The aqueous layer was removed, and the oily layer was thoroughly mixed with 800 ml of ion-exchanged water for 1 hour and allowed to stand. The aqueous layer was removed, and the oily layer was concentrated under reduced pressure in a rotary evaporator. In this way, 103 g of low molecular weight polyisoprene were obtained as a colorless, transparent liquor having a viscosity of 24 cp at 30° C. The number average molecular weight was 410 on determining by means of a vapor pressure osmometer. The infrared analysis according to the Morero's method showed that the microstructure of the polymer consisted of 42% of the cis-1,4 structure, 35.2% of the trans-1,4 structure, 19.8% of the 3,4 structure and 2.7% of the 1,2 structure. Further, it was confirmed that the value of the 3,4 structure was due to the absorption of the vinylidene group which resulted from the dehydrogenation of one propylene molecule connected to the ends of the polymer chains. Thus, more than 90% of isoprene was polymerized in the 1,4-polymerization form.

Raney nickel R-200 (produced by Nikko Rikagaku Sangyo Co., Ltd.) was activated, followed by deaeration and dehydration, and stored in a Schlenk's tube replaced by nitrogen gas. To a 200-ml stainless steel autoclave were added 5 g of the Raney nickel, 75 ml of the above obtained liquid polyisoprene and 75 ml of cyclohexane, and hydrogen gas was charged therein from a hydrogen bomb until a pressure gauge indicated 25 kg/cm$^2$. The contents were heated to 150° C. in an oil bath while being mixed, and mixation was further continued at 150° C. under 25 kg/cm$^2$ for 30 hours so as to complete the hydrogenation. After cooling, the pressure in the autoclave was released to atmospheric pressure, and the catalyst was removed centrifugally to obtain a colorless, transparent liquor. The liquor was concentrated under reduced pressure in a rotary evaporator to remove the solvent, whereby 74 ml of a colorless, transparent liquor having a viscosity of 35 cp at 30° C. were obtained. The liquid polyisoprene thus hydrogenated showed approximately the same NMR and infrared spectrum charts as those of squalane. On comparison of the NMR charts, the ratios represented by:

$$\frac{\text{The area of signals of the protons from the methyl groups}}{\text{The area of signals of the total protons}}$$

were 0.39 and 0.40 respectively for squalane and the hydrogenated liquid polyisoprene. Consequently, it became clear that the hydrogenated liquid polyisoprene has almost the same structure as that of squalene.

Fractional distillation of 10 g of the hydrogenated product by the use of a molecular distillation apparatus gave 3.5 g of the first fraction (b.p., lower than 120° C./1 mmHg), 3.2 g of the second fraction (b.p., 140° C./1 mmHg to 250° C./0.2 mmHg) and 3.3 g of the residue. As the first fraction has very slight irritation to skin, it is excluded from this invention.

EXAMPLE 2

The atmosphere in a 1,5-liter stainless steel autoclave (20 kg/cm$^2$ proof) equipped with a stirrer was replaced by nitrogen gas. Thereafter, 300 ml of anhydrous toluene and 136 g of anhydrous isoprene were charged into the autoclave under the stream of nitrogen. The mixture was cooled to −50° C., and 4 ml of a toluene solution containing 0.1 mol/liter of nickel naphthenate, 4 ml of a toluene solution containing 1 mol/liter of ethylaluminum sesquichloride, 20 ml of a toluene solution containing 0.02 mol/liter of triphenyl phosphine and 64 g of propylene were added thereto, followed by polymerization at 60° C. for 6 hours. The polymerization was stopped in the same manner as in Example 1. Removal of the catalyst was also carried out in the same manner as in Example 1, followed by concentration under reduced pressure in a rotary evaporator. In this way, 73 g of low molecular weight polyisoprene were obtained as a colorless, transparent liquor having a viscosity of 983 cp at 30° C. The number average molecular weight was 540 on determining by means of a vapor pressure osmometer. The infrared analysis according to the Morero's method showed that the microstructure of the polymer consisted of 43.6% of the cis-1,4 structure, 36.9% of the trans-1,4 structure, 19.0% of the 3,4 structure and 0.5% of the vinyl structure. Further, it was confirmed that the 3,4 structure was due to the absorption of the vinylidene group which resulted from the dehydrogenation of one propylene molecule connected to the ends of the polymer chains.

Hydrogenation was carried out by replacing the atmosphere in a 200-ml stainless steel autoclave by nitrogen gas, charging 65 ml of the above obtained liquid polyisoprene, 5 g of Raney nickel R-200 as activated and 75 ml of cyclohexane into the autoclave, and mixing the contents at 150° C. for 30 hours while maintaining the hydrogen pressure in the autoclave at 25 kg/cm$^2$. After cooling, the catalyst was centrifugally removed to obtain a colorless, transparent liquor. The liquor was concentrated under reduced pressure in a rotary evaporator to remove the solvent, whereby 64 ml of a colorless, transparent liquor having a viscosity of 1,050 cp at 30° C. were obtained. The iodine value, the hydroxyl value and the acid value were all zero.

EXAMPLE 3

A rotator for a magnetic stirrer was placed in a 500-ml four-necked flask, and the mouths of the flask were equipped with ampoules containing 28.2 g of anhydrous naphthalene, 200 ml of anhydrous tetrahydrofuran, 40 ml of anhydrous isoprene and 1.38 g of metallic lithium, respectively. After completely replacing the atmosphere in the flask by nitrogen gas, the ampoule containing metallic lithium was opened by a magnetic hammer to allow the lithium to fall into the flask. Next, tetrahydrofuran and naphthalene were allowed to fall in the same manner as above. On mixing the contents in the flask at room temperature for 17 hours, a deep green complex of lithium-naphthalene was formed. After cooling to −70° C., isoprene was added, and the mixture was stirred at room temperature for 2 hours, whereby the reaction solution turned to yellow brown. The tetrahydrofuran was removed from the reaction solution under reduced pressure, and then 100 ml of anhydrous n-hexane and 100 ml of cyclohexane were added thereto under the stream of nitrogen gas. After cooling to −40° C., 95 ml of isoprene were added, and polymerization was carried out at 50° C. for 3 hours. The metallic lithium was removed from the product, in the same manner as in Example 1, by washing the reaction mixture with an aqueous hydrochloric acid solution. After neutralization and washing with water, the separated oil layer was concentrated under reduced pressure in a rotary evaporator to give low molecular weight polyisoprene. By the analysis according to the Morero's method, the microstructure of the resulting polymer was found to consist of 85% of the cis-1,4 structure and 15% of the 3,4 structure. The molecular weight determined by means of a vapor pressure osmometer was 760.

In the same manner as in Example 1, 64 g of the thus obtained liquid polyisoprene were hydrogenated in a 200-ml stainless steel autoclave using 5 g of Raney nickel R-200 and 75 ml of cyclohexane. The hydrogenation was carried out at 150° C. for 30 hours with stirring, while keeping the hydrogen pressure in the autoclave at 30 kg/cm$^2$. After cooling, the catalyst was centrifugally removed to obtain a colorless, transparent liquor. The liquor was concentrated under reduced pressure in a rotary evaporator to obtain 63 g of a colorless and odorless, transparent liquor having a viscosity of 130 cp at 30° C. The iodine value, the hydroxyl value and the acid value of the liquor were all zero.

EXAMPLE 4

Preparation of the catalyst, the polymerization and the after-treatment was carried out in the same manner as in Example 3 using 7.05 g of anhydrous naphthalene, 200 ml of anhydrous tetrahydrofuran, 25 ml of anhydrous isoprene and 0.345 g of metallic lithium to give low molecular weight polyisoprene. By the analysis according to the Morero's method, the microstructure of the obtained polymer was found to consist of 88% of the cis-1,4 structure and 12% of the 3,4 structure. The molecular weight determined by means of a vapor pressure osmometer was 2,800.

In the same manner as in Example 1, 64 g of the liquid polyisoprene was hydrogenated at 150° C. for 30 hours using 5 g of Raney nickel R-200 and 75 ml of cyclohexane while keeping the hydrogen pressure at 30 kg/cm$^2$. After cooling, the reaction mixture was centrifuged in order to remove the catalyst, and concentrated under reduced pressure in a rotary evaporator to obtain 63 g of a colorless, transparent liquor. The liquor was colorless and odorless and had a viscosity of 3,600 cp. The iodine value, the hydroxyl value and the acid value of the liquor were all zero.

EXAMPLE 5

The comparison of physical properties between squalene and the hydrogenated low molecular weight polyisoprene (second fraction obtained in Example 1) is shown in the following table:

Table 1

|  | Second fraction in Example 1 | Squalane |
| --- | --- | --- |
| Number average molecular weight | 407 | 417 |
| Viscosity at 30° C (cp) | 27 | 22 |
| Acid value | 0 | 0 |
| Iodine value (Wijs method) | 0 | 0 |
| Hydroxyl value | 0 | 0.2 |
| Odor | no | no |
| Appearance | colorless, transparent | colorless, transparent |

Cold cream containing the hydrogenated polyisoprene in Table 1 were formulated according to the following recipe:

|  | Part(s) by weight |
| --- | --- |
| Liquid paraffin | 20 |
| Beeswax | 15 |
| Hydrogenated polyisoprene | 13 |
| Lanolin | 5 |
| Isopropyl myristate | 4 |
| Monoglyceride | 3 |
| Polyoxyethylene sorbitan monooleate | 3 |
| Ethylene glycol | 4 |
| Sodium hydroxide | 0.1 |
| Water | 35 |
| Perfume | 0.5 |

The cold cream thus formulated was the same as that obtained using squalene in place of the hydrogenated polyisoprene in color, odor, long-term stability, non-irritativeness, spread, stiffness and touch.

EXAMPLE 6

Lipstick containing the same hydrogenated polyisoprene as in Example 5 was formulated according to the following recipe:

|  | Part(s) by weight |
| --- | --- |
| Beeswax | 15 |
| Hydrogenated polyisoprene | 7 |
| G wax | 3 |
| Carnauba wax | 3 |
| Lanolin | 5 |
| Castor oil | 5 |
| Hardened cotton-seed oil | 5 |
| Stearyl alcohol | 10 |
| Pigment and perfume | 7 |

The lipstick thus formulated exhibited the same luster and spread as those of the lipstick formulated using squalene in place of the hydrogenated polyisoprene.

EXAMPLE 7

Hygienic cream containing the same hydrogenated polyisoprene as in Example 5 was formulated according to the following recipe:

|  | Part(s) by weight |
|---|---|
| Hydrogenated polyisoprene | 10 |
| Stearic acid | 8 |
| Palmitic acid | 2 |
| Lanolin | 3 |
| Stearyl alcohol | 5 |
| Diglyceride | 3 |
| Polyoxyethylene sorbitan monopalmitate | 3 |

The hygienic cream thus formulated exhibited the same spread and smoothness as those of the hygienic cream formulated using squalene in place of the hydrogenated polyisoprene.

EXAMPLE 8

Low molecular weight polyisoprene was prepared under completely the same conditions of polymerization and after-treatment as in Example 1 in order to check the reproducibility, whereby 103 g of a colorless, transparent liquor having a viscosity of 18 cp at 30° C. were obtained. On determining the molecular weight by means of a vapor pressure osmometer, the number average molecular weight was 390.

Hydrogenation of the liquid polyisoprene was carried out under completely the same conditions as in Example 1. After completion of the hydrogenation, the reaction mixture was cooled and the pressure was released to atmospheric pressure. The catalyst was centrifugally removed to obtain a colorless, transparent liquor. In order to remove the solvent, the liquor was concentrated under reduced pressure in a rotary evaporator, whereby 74 ml of a colorless, transparent liquor were obtained. The viscosity was 30 cp at 30° C. The liquid polyisoprene thus hydrogenated exhibited almost the same NMR and infrared spectrum charts as those of squalene. On comparison of the NMR charts, the ratios represented by:

$$\frac{\text{The area of signals of the protons from the methyl groups}}{\text{The area of signals of the total protons}}$$

were 0.39 and 0.40 respectively for squalene and the hydrogenated liquid polyisoprene. Consequently, it became clear that the hydrogenated liquid polyisoprene has almost the same structure as that of squalene.

Fractional distillation of 10 g of the hydrogenated product by the use of a molecular distillation apparatus gave 3.1 g of the first fraction (b.p., lower than 190° C./1 mmHg) and 6.9 g of the residue. The viscosity of the residue was compared with that of squalene and of the polymer of octene-1 as shown in Table 2.

As seen from Table 2, the hydrogenated polyisoprene as a lubricating oil has a high viscosity index and is a free flowing, low viscous liquid even at extremely low temperatures. This means that the hydrogenated polyisoprene passes the standards of the lubricating oil for jet engines specified by the American Military Standards. Thus, the lubricating oil of the present invention has almost the same flowing property as that of squalene and is very superior as a lubricating oil for jet engines. The polymer of octene-1 is inferior to the lubricating oil of the present invention in viscosity index and flow point. Particularly, the viscosity at −40° C. of the octene-1 polymer is close to the upper limit of the said Standards, which clearly means that the polymer has a very poor viscosity performance at low temperatures.

Table 2

| Properties MIL-H 83282 Standard | Hydrogenated polyisoprene | Squalane | Polymer of octene-1 |
|---|---|---|---|
| Viscosity, 210° F (cp) more than 3.5 | 10 | 4.8 | 4.3 |
| Viscosity, 100° F (cp) more than 16.5 | 32 | 20 | 20.8 |
| Viscosity, −40° F (cp) less than 3000 | 420 | 340 | 2800 |
| Viscosity index more than 120 | 140 | 140 | 125 |
| Flash point (° F) more than 400 | 425 | 425 | 412 |
| Flow point (° F) less than −65 | less than −85 | less than −85 | −70 |

Table 3 shows that the synthetic lubricating oil comprising the hydrogenated polyisoprene of the present invention is much superior as a lubricating oil for precision machines to commercially available products selected from those which are best as a synthetic lubricating oil for precision machines.

Table 3

| Physical properties | The residue in Example 8 | Reference example |  |  |
|---|---|---|---|---|
|  |  | Commercial product 1 | Commercial product 2 | Commercial product 3 |
| Flash point (° C) | 218 | 173 | 211 | 216 |
| Viscosity at 30° C (cp) | 52 | 20.7 | 36.5 | 102 |
| Viscosity index | 140 | 125 | 134 | 123 |
| Flow point (° C) | less than −65 | −22.5 | −37.5 | −37.5 |

The above commercially available product are in use for public telephones, watches, electric power meters and various equipments and are regarded as important as a lubricating oil having a particularly superior viscosity performance at low temperatures. However, the lubricating oil of the present invention is much superior to those commercial products in that performance. For example, the oil has a viscosity of as low as 510 centistokes even at −40° C., while those commercial products solidify at −37.5° C. Further, the oil of the present invention has a viscosity index of 140, which means that the oil is superior to those commercial products in the viscosity performance.

The octene-1 polymer as described for comparison in Table 2 was synthesized by the following method:

In a 2,000-ml four-necked flask, 200 ml of ethyl ether were charged, and 17 g of aluminum chloride were dissolved in the ether. Thereafter, 3.1 g of lithium hydride was added to prepare a catalyst, and a large proportion of ethyl ether was removed under reduced pressure. To the flask were added 800 ml of octene-1 and 25 g of titanium tetrachloride, and the reaction was carried out at 100° to 200° C. for 4 hours. After completion of the reaction, ammonia gas was blown into the reaction solution, and the resulting precipitates were filtered off to remove the catalyst. The resulting reaction solution was distilled under reduced pressure to remove the unreacted octene-1 and the dimers thereof.

Hydrogenation was then carried out at 150° C. and at a hydrogen pressure of 20 kg/cm² using Raney nickel catalyst. After the hydrogenation, the catalyst was removed to obtain 490 g of the oligomer. The content of tri- to pentamers in the oligomer was 80%.

What is claimed is:

1. A method for preparation of synthetic saturated oils, which comprises hydrogenation of low molecular weight polyisoprene having the 1,4 structure of at least 70% in the main chains and a number average molecular weight of about 290 to 3,000.

2. The method according to claim 1, wherein the hydrogenation is carried out by treatment with hydrogen in the presence of a hydrogenation catalyst.

3. The method according to claim 2, wherein the hydrogenation catalyst is nickel, palladium or platinum.

4. The method according to claim 2, wherein the hydrogenation is carried out at a temperature of about 50° to 350° C. under a hydrogen pressure of about 5 to 300 kg/cm².

5. The method according to claim 4, wherein the hydrogenation is carried out within a period of about 1 to 100 hours.

6. The method according to claim 1, followed by fractional distillation.

7. A synthetic saturated oil prepared by the method according to claim 1.

8. A synthetic saturated oil which is substantially representable by the formula:

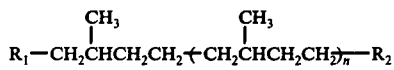

wherein $R_1$ is hydrogen or alkyl having 1 to 8 carbon atoms, $R_2$ is hydrogen, ethyl or isopropyl and $R_1$ and $R_2$ are not hydrogens at the same time, and $n$ is an integer of 3 to 40.

9. The synthetic saturated oil according to claim 8, wherein $n$ is an integer of 4 to 20.

10. A lubricating oil comprising the synthetic saturated oil according to claim 7 combined with at least one lubricating oil additive.

11. A cosmetic comprising the synthetic saturated oil according to claim 7 combined with at least one cosmetic oil additive.

12. A colorless, transparent and odorless, liquid synthetic oil having a boiling point at 760 mmHg $\geq 250°$ C., a specific gravity of $0.80 \leq d^{20} \leq 0.92$, a refractive index of $1.44 \leq n_D^{20} \leq 1.50$, and a viscosity of $5 \text{ cp} \leq \eta^{25°} \text{C.} \leq 10^5 \text{ cp}$, said oil being substantially represented by the formula:

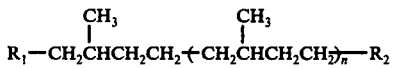

wherein $R_1$ is hydrogen or alkyl having 1 to 8 carbon atoms, $R_2$ is hydrogen, ethyl or isopropyl and $R_1$ and $R_2$ are not hydrogens at the same time, and $n$ is an integer of 3 to 40.

13. The liquid synthetic oil according to claim 12, wherein $n$ is an integer of 4 to 20.

* * * * *